United States Patent [19]  [11] Patent Number: 4,621,087
Wick et al.  [45] Date of Patent: Nov. 4, 1986

[54] ANTI-ANOXIC FURO- OR PYRROLO-PYRIDINE COMPOUNDS AND PHARMACEUTICAL COMPOSITIONS CONTAINING THEM

[75] Inventors: Alexander Wick, Saint Nom-La Bretèche; Jonathan Frost, Wissous; Patrick Lardenois, Bourg-la-Reine, all of France

[73] Assignee: Synthelabo, Paris, France

[21] Appl. No.: 748,765

[22] Filed: Jun. 26, 1985

[30] Foreign Application Priority Data

Jun. 27, 1984 [FR] France ................................ 84 10108

[51] Int. Cl.[4] ................ A61K 31/44; C07D 491/048; C07D 471/04
[52] U.S. Cl. ................................ 514/300; 514/302; 546/300; 546/302
[58] Field of Search ............. 546/113, 115; 514/300, 514/302

[56] References Cited

U.S. PATENT DOCUMENTS 3,992,544 11/1976 Archibald et al. ............. 424/263
4,075,215 2/1978 Castaigne .................... 260/294.3

FOREIGN PATENT DOCUMENTS 2138817A 4/1983 United Kingdom ............ 546/115

Primary Examiner—Henry R. Jiles
Assistant Examiner—Bernard I. Dentz
Attorney, Agent, or Firm—Wegner & Bretschneider

[57] ABSTRACT

Pyridine derivatives of the general formula (I)

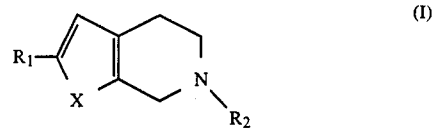

in which X is —O— or —NH—, $R_1$ is a phenyl group optionally substituted by one or two halogen atoms or a methyl, ethyl, trifluoromethyl, methoxy or phenyl group or, when $R_2$ is not a benzyl group, an amino group, or is a naphthyl or benzodioxanyl group, and $R_2$ is hydrogen or a benzyl group, or when X is —O—, $R_2$ can also be a methyl or ethyl group, and their pharmaceutically acceptable acid addition salts are useful as antianoxics.

9 Claims, No Drawings

ANTI-ANOXIC FURO- OR PYRROLO-PYRIDINE COMPOUNDS AND PHARMACEUTICAL COMPOSITIONS CONTAINING THEM

The present invention relates to 4,5,6,7-tetrahydrofuro- or -1-H-pyrrolo[2,3-c]pyridine derivatives.

The invention provides pyridine derivatives of formula

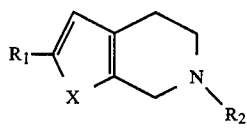

(I)

in which X is —O— or —NH—, $R_1$ is a phenyl group optionally substituted by one or two halogen atoms or a methyl, ethyl, trifluoromethyl, methoxy or phenyl group or, when $R^2$ is not a benzyl group, an amino group, or is a naphthyl or benzodioxanyl group, and $R_2$ is hydrogen or a benzyl group, or when X is —O—, $R_2$ can also be a methyl or ethyl group.

The pyridine derivatives of formula (I) are shown as free bases and the invention also provides their pharmaceutically acceptable acid addition salts.

The preferred compounds of the invention are those wherein $R_2$ is hydrogen. Other preferred compounds are those wherein X is —O— and $R_2$ is methyl or ethyl.

The compounds of the invention can be prepared by a process which comprises:

(i) cyclising a compound of formula (II)

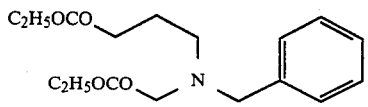

(II)

in the presence of an alkali metal hydride, (ii) reacting the product obtained, of formula (III)

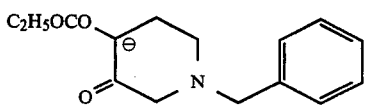

(III)

with an acetophenone of formula (IV)

(IV)

in which $R_1$ is as hereinbefore defined or is nitrophenyl, to provide a compound of formula (V)

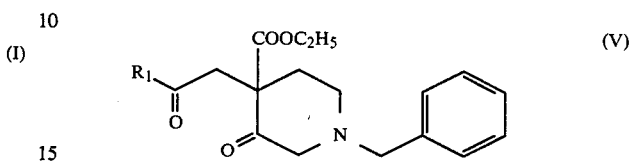

(V)

(iii) then, depending on the compound which it is desired to prepare, either (a) cyclising the compound (V) in the presence of ammonium acetate and acetic acid and treating the compound obtained, of formula (VI)

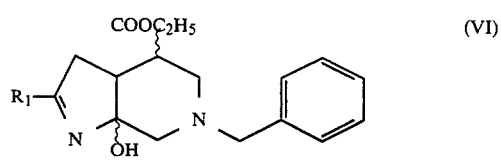

(VI)

first with caustic soda and then with hydrochloric acid to provide a pyrrolopyridine compound of formula (I) in which X is —NH— and $R_2$ is benzyl or (b) cyclising the compound (V) in the presence of a strong acid to provide a furopyridine compound of formula (I) in which X is —O— and $R_2$ is benzyl, (iv) if desired debenzylating the compound (I) thus obtained and simultaneously reducing the aminophenyl the group $R_1$ when it represents nitrophenyl to provide a compound of formula (I) in which $R_2$ is hydrogen and (v) also if desired alkylating a compound of formula (I) in which $R_2$ is hydrogen to provide a compound in which $R_2$ is methyl or ethyl, and (vi) if desired converting the pyridine derivative of formula (I) obtained from (iii), (iv) or (v) into a pharmaceutically acceptable acid addition salt in a manner known per se.

This process is illustrated by the scheme given below:

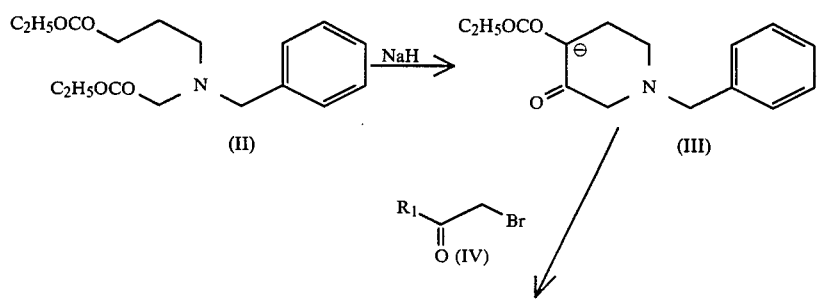

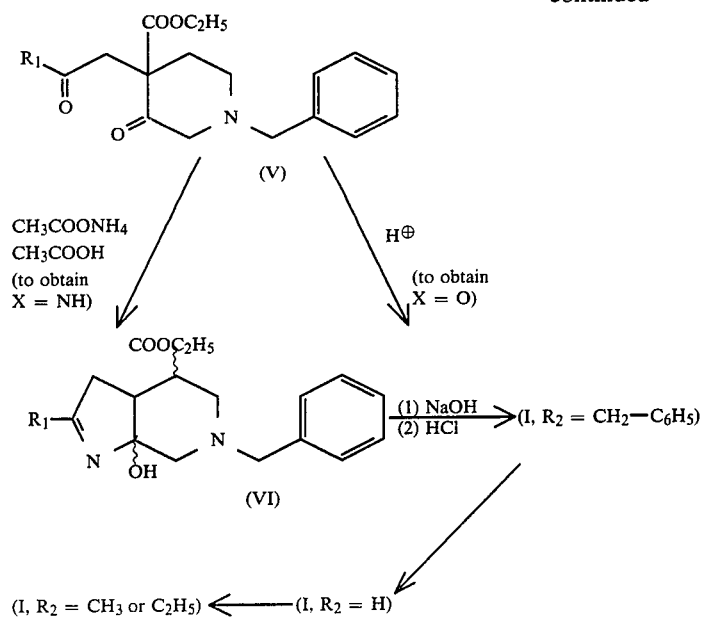

The first stage of the process consisting in cyclising a diester of formula (II), preferably the diethyl ester, in the presence of an alkali metal hydride, suitably at the refluxing temperature of a solvent such as toluene. The compound of formula (III) thus obtained is then reacted with an acetophenone of formula (IV) bearing a labile group such as a bromine atom, and suitably substituted with $R_1$ on the benzene ring. This reaction is preferably performed at room temperature.

According to the compound (I) to be prepared, that is to say according to whether X denotes —O— or —NH—, the compound of formula (V) obtained is then subjected to either of two types of reaction.

If it is desired to prepare a pyrrolopyridine derivative (X=NH), a cyclisation is first performed in the presence of ammonium acetate and acetic acid, and the resulting compound of formula (VI) is then decarboxylated and dehydrated by being treated first with caustic soda and then with hydrochloric acid.

If it is desired to prepare a furopyridine derivative (X=O), compound (V) is subjected to cyclisation in a strong acid medium.

Compounds of formula (I) thus obtained necessarily bear an $R_2$ substituent which is a benzyl group. For this reason, if it is so desired, debenzylation can be performed to obtain a compound (I) in which $R_2$ is hydrogen for example by performing a catalytic hydrogenation or else by first reacting the benzylated compound (I) with 2,2,2-trichloroethyl chloroformate and fragmenting the carbamate obtained with zinc in the presence of acetic acid.

To prepare the compounds in the formula (I) in which $R^1$ denotes an aminophenyl group, an acetophenone of formula (IV) is used in which $R_1$ is a nitrophenyl group. The nitro group thus introduced is reduced to an amino group during the final debenzylation by catalytic hydrogenation (benzyl group $R_2$ replaced by a hydrogen atom).

The starting compound of formula (II) can be prepared, for example, by the action of ethyl 4-bromobutanoate on ethyl phenylmethylaminoacetate in the presence of a base such as 2,6-dimethyl pyridine.

In the case of the compounds of formula (I) in which X denotes an oxygen atom and $R_2$ denotes a hydrogen atom, instead of the N-benzylated starting derivative of the formula (II), the corresponding N-benzoylated derivative can be used. The benzoyl group is then eliminated during the cyclisation reaction, in acid medium, of the corresponding compound of formula (V) (that is to say benzoylated instead of benzylated), and a final debenzylation is no longer necessary.

Finally, the compounds (I) in the formula of which $R_2$ denotes a methyl or ethyl group are obtained by alkylation starting from the compounds in which $R_2$ is hydrogen, for example by the action of a methyl or ethyl halide, or else by means of formic acid and formaldehyde (in the case of a methyl group), or by acetylation followed by reduction (in the case of an ethyl group).

The Examples which follow illustrate the invention. The structures of the compounds prepared were confirmed by microanalysis and the IR and NMR spectra.

EXAMPLE 1

2-Phenyl-6-phenylmethyl-4,5,6,7-tetrahydro-1H-pyrrolo[2,3-c]pyridine and its hydrochloride (a) To a solution of 20 g (0.065 mole) of ethyl 4-[(2-ethoxy-2-oxoethyl)(phenylmethyl)amino]butanoate in 440 ml of toluene there are added 3.25 g (0.065 mole) of a 50% strength suspension of sodium hydride in mineral oil, the mixture is heated to reflux and a few drops of anhydrous ethanol are added. The reaction is exothermic and a solution is obtained which is maintained for a further 4 hours under reflux and then cooled in an ice bath.

(b) To the solution prepared above, 14 g (0.070 mole) of 1-bromoacetophenone are added and the mixture is stirred overnight at room temperature. 200 ml of water are added, the mixture is stirred, the organic phase is separated, and this is dried and evaporated. An oil remains, and this is used as such in the following stage.

(c) To 24.6 g (0.065 mole) of the oil obtained above there is added a solution of 15 g (0.195 mole) of ammonium acetate in 120 ml of acetic acid, and the mixture is stirred for 5 hours at room temperature. It is poured onto a cooled mixture of 300 ml of water and ice, 160 ml of concentrated ammonia solution and 50 ml of ethyl acetate. The whole mixture is stirred for 10 minutes at room temperature, and the precipitate formed is filtered, washed with ethanol and dried.

(d) 10.4 g of the solid obtained above are introduced into a mixture of 200 ml of water, 200 ml of ethanol and 200 ml of caustic soda, and the mixture is stirred at room temperature for 3 hours. Some slight turbidity is removed by filtration and, in an ice-bath, 200 ml of concentrated hydrochloric acid are added dropwise to the filtrate. The mixture is stirred for 2 hours at room temperature and the precipitate then filtered, washed with water and ethanol, dried, recrystallised in 95% strength ethanol and dried.

Melting point: 236°–238° C.

EXAMPLE 2

2-(4-Methoxyphenyl)-6-phenylmethyl-4,5,6,7-tetrahydro-1H-pyrrolo[2,3-c]pyridine and its hydrochloride (a) A solution of 0.1 mole of the anion of ethyl-3-oxo-1-phenylmethyl-4-piperidinecarboxylate is prepared according to Example 1(a) above, in 700 ml of toluene.

(b) To the solution thus prepared, 22.9 g (0.1 mole) of 1-bromo-4'-methoxyacetophenone are added and the mixture is stirred overnight at room temperature. 100 ml of water are added, the mixture is stirred for 15 minutes, and the organic phase is separated, dried and evaporated. An oil remains, and this is used as such in the following stage.

(c) To 26.6 g (0.065 mole) of the oil obtained above there is added a solution of 15 g (0.195 mole) of ammonium acetate in 120 ml of acetic acid. The preparation is completed as described in Example 1(c) above, and a solid is collected which is used as such.

(d) 8.4 g (0.0205 mole) of this solid are introduced into a mixture of 170 ml of water, 170 ml of ethanol and 170 ml of caustic soda, and the mixture is stirred for 3 h 30 min at room temperature. It is cooled in an ice bath, 170 ml of concentrated hydrochloric acid are added and the mixture is left overnight at room temperature. The precipitate is filtered, washed with water and then acetone, dried and recrystallised in an ethanol/water mixture. After being dried, pale blue-green crystals remain.

Melting point: 237°–238° C.

EXAMPLE 3

2-(4-Bromophenyl)-6-phenylmethyl-4,5,6,7-tetrahydro-1H-pyrrolo[2,3-c]pyridine and its hydrochloride (a) A solution of 0.2 mole of the anion of ethyl-3-oxo-1-phenylmethyl-4-piperidinecarboxylate is prepared according to Example 1(a) above.

(b) To the solution thus prepared, 55.6 g (0.2 mole) of 1,4'-dibromoacetophenone are added and the mixture is left to react overnight. 200 ml of water are then added, the mixture is stirred and the organic phase is separated by decantation, dried and evaporated. An oil remains.

(c) 45.8 g (0.1 mole) of this oil are introduced into a solution of 23 g (0.3 mole) of ammonium acetate and 180 ml of acetic acid, and the mixture is stirred at room temperature for 3 hours. While cooling is applied, the mixture is then poured into a solution of 600 ml of water and ice, 280 ml of concentrated ammonia solution and 50 ml of ethyl acetate. The mixture is stirred for several minutes, and the precipitate is filtered, washed with petroleum ether and dried.

Melting point: approximately 160° C.

(d) 18.7 g (0.041 mole) of this product are dissolved in a mixture of 180 ml of ethanol, 180 ml of water and 180 ml of caustic soda, the mixture is stirred for 6 hours at room temperature, some slight turbidity is filtered off, the mixture is cooled and 180 ml of concentrated hydrochloric acid are added dropwise. After 45 minutes' stirring, the precipitate is filtered, washed with water and then ether, dried, recrystallised in a 50:50-ethanol/water mixture and dried.

Melting point: 264°–266° C. with decomposition.

EXAMPLE 4

2-(4-Fluorophenyl)-6-phenylmethyl-4,5,6,7-tetrahydro-1H-pyrrolo[2,3-c]pyridine and its hydrochloride (a) A solution of the anion of ethyl 3-oxo-1-phenylmethyl-4-piperidinecarboxylate is prepared from 30.7 g (0.1 mole) of ethyl 4-[(2-ethoxy-2-oxoethyl)(phenylmethyl)amino]butanoate according to the method given in Example 1(a) above.

(b) To the cooled solution, 21.7 g (0.1 mole) of 1-bromo-4'-fluoroacetophenone are added, and the mixture is left to react overnight at room temperature. The organic phase is separated, washed, dried and evaporated. An oil remains, and this is used as such.

(c) 19.9 g (0.05 mole) of this oil are introduced into a solution of 11.5 g of ammonium acetate in 95 ml of acetic acid and the mixture is stirred for 3 h 30 min at room temperature. It is then poured into a solution of 300 ml of ice, 140 ml of concentrated ammonia solution and 25 ml of ethyl acetate. The mixture is stirred for 15 minutes while being cooled, and the precipitate is filtered, washed with water and then ether and dried.

Melting point: 176° C.

(d) To 10.5 g (0.0264 mole) of this solid, 100 ml of ethanol, 100 ml of water and 100 ml of caustic soda are added, and the mixture is left to react overnight at room temperature. To the solution obtained, 100 ml of concentrated hydrochloric acid are then added dropwise, and the mixture is stirred for a further 2 hours. The precipitate is filtered, washed with water and ether, dried, recrystallised in 350 ml of an ethanol/water mixture containing 1% of concentrated hydrochloric acid and dried.

Melting point: 246°–248° C.

EXAMPLE 5

2-(4-Methoxyphenyl)-4,5,6,7-tetrahydro-1H-pyrrolo[2,3-c]pyridine and its hydrochloride A mixture is prepared of 7.1 g (0.02 mole) of the compound obtained according to Example 2, 70 ml of acetic acid, 70 ml of water and 0.7 g of palladinised charcoal (10% palladium), and subjected for 7 hours to hydrogenation at a pressure of 0.35 Mpa at 50° C. The mixture was left undisturbed overnight and subjected again to hydrogenation under the same conditions for 5 hours. The catalyst is separated, the filtrate is evaporated and the crystallised residue is taken up in 10 ml of ethanol containing 10% of concentrated hydrochloric acid and stirred for 15 minutes in an ice bath, and the solid is filtered, washed with ether, recrystallised in 100 ml of ethanol containing 1% of concentrated hydrochloric acid and dried.

Melting point: 235° C. with decomposition.

EXAMPLE 6

2-Phenyl-4,5,6,7-tetrahydro-1H-pyrrolo[2,3-c]pyridine and its hydro-chloride To 1 g (0.003 mole) of the hydrochloride obtained according to Example 1, there are added 10 ml of acetic acid, 10 ml of water and 100 ml of palladinised charcoal (5% of palladium), and the mixture is subjected to hydrogenation at 0.35 Mpa for 7 hours at 50° C. The catalyst is filtered and the filtrate evaporated, the solid residue taken up in 10 ml of ethanol containing 1% of concentrated hydrochloric acid, the precipitate is filtered, washed with ether and dried, and the base is liberated in ethyl acetate by means of ammonia solution and purified by chromatography on silica, eluting with an 8:2-chloroform/methanol mixture.

Melting point: 179°–181° C.

The hydrochloride of this is prepared in ethanol.
Melting point: 249°–251° C.

EXAMPLE 7

2-(4-Methoxyphenyl)-6-phenylmethyl-4,5,6,7-tetrahydrofuro[2,3-c]pyridine and its hydrochloride (a) The anion of ethyl 3-oxo-1-phenylmethyl-4-piperidinecarboxylate is prepared according to Example 1(a) above.

(b) Ethyl 4-[2-(4-methoxyphenyl)-2-oxoethyl]-3-oxo-1-phenylmethyl-4-piperidinecarboxylate is prepared according to Example 2(b) above.

(c) 18 g (0.044 mole) of the oil thus obtained is dissolved in 18 ml of ethanol, 270 ml of concentrated hydrochloric acid are added, and the mixture is heated to reflux for 1 h 30 min and then cooled in ice. The precipitate formed is filtered, washed with water, then ether and then chloroform, recrystallised in a 75:25-ethanol/water mixture and dried.

Melting point: 252°–253° C.

EXAMPLE 8

2-(4-Methylphenyl)-6-phenylmethyl-4,5,6,7-tetrahydrofuro[2,3-c]pyridine and its hydrochloride (a) The anion of ethyl 3-oxo-1-phenylmethyl-4-piperidinecarboxylate is prepared according to Example 1(a) above.

(b) The solution obtained is cooled, 21.3 g (0.1 mole) of 1-bromo-4'-methylacetophenone dissolved in 50 ml of toluene are added, and the mixture is left to react overnight at room temperature. 100 ml of water are added, the mixture is stirred and the organic phase is separated and evaporated. An oil remains and this is used as such.

(c) The oil thus obtained is dissolved in 40 ml of ethanol, 500 ml of concentrated hydrochloric acid are added and the mixture is heated to reflux for 1 h 30 min and cooled in ice. The precipitate formed is filtered, washed with chloroform and then ether, dried and recrystallised in ethanol. A white product remains.

Melting point: 251°–253° C.

EXAMPLE 9

2-(4-Bromophenyl)-6-phenylmethyl-4,5,6,7-tetrahydrofuro[2,3-c]pyridine and its hydrochloride (a) A solution of the anion of ethyl 3-oxo-1-phenylmethyl-4-piperidinecarboxylate is prepared according to the method given in Example 1(a) above.

(b) Ethyl 4-[2-(4-bromophenyl)-2-oxoethyl]-3-oxo-1-phenylmethyl-4-piperidinecarboxylate is prepared according to the method given in Example 3(b) above.

(c) 45.8 g (0.1 mole) of the oil thus obtained is dissolved in 40 ml of ethanol, 500 ml of concentrated hydrochloric acid are added and the mixture is heated to reflux for 2 h 30 min. The mixture is cooled, and the brown precipitate is filtered, washed with chloroform and then ether, recrystallised in a 1:1-ethanol/water mixture and dried. A white product remains.

Melting point: 263°–265° C. with decomposition.

EXAMPLE 10

2-(4-Methoxyphenyl)-4,5,6,7-tetrahydrofuro[2,3-c]pyridine and its hydrochloride A suspension is prepared of 11 g (0.309 mole) of the compound prepared according to Example 7 in 100 ml of acetic acid and 100 ml of water. 250 mg of palladinised charcoal (5% of palladium) are added and the mixture is subjected to hydrogenation at approximately 0.35 Mpa for 7 hours at 50° C. The catalyst is filtered off, the filtrate is evaporated and the crystallised residue taken up in 25 ml of ethanol containing 1% of concentrated hydrochloric acid, and the base is liberated therefrom and purified by chromatography on silica, eluting with an 8:2-chloroform/methanol mixture. The pure base melts at 112° C. The hydrochloride of this is prepared in 100 ml of ethanol containing 1% of concentrated hydrochloric acid, the mixture is heated to reflux to recrystallise the salt, and this is filtered and dried.

Melting point: 226°–228° C.

EXAMPLE 11

2-(4-Bromophenyl)-4,5,6,7-tetrahydrofuro[2,3-c]pyridine and its hydrochloride 5.8 g (0.0157 mole) of the compound prepared according to Example 9 are introduced into 120 ml of toluene, 6.35 ml (0.0471 mole) of 2,2,2-trichloroethyl chloroformate are added and the mixture is heated under reflux for 12 hours. The mixture is left to stand overnight, a further 2 ml of 2,2,2-trichloroethyl chloroformate are added and the mixture is brought back to reflux for 4 hours. The solvent is driven off and the residual 2,2,2-trichloroethyl 2-(4-bromophenyl)-4,5,6,7-tetrahydrofuro[2,3-c]pyridine-6-carboxylate is taken up in 75 ml of acetic acid, 5 g of zinc powder are added and the mixture is stirred for 7 hours and left to stand.

The mixture is filtered, the filtrate is evaporated and the residue is taken up in 100 ml of water and extracted with ethyl acetate after ammonia solution has been added. The organic phases are evaporated and purified on silica with an 8:2-chloroform/methanol mixture, the purified base is dissolved in 5 ml of ethanol and a few drops of concentrated hydrochloric acid are added. The precipitate is filtered and recrystallised in ethanol containing 1% of concentrated hydrochloric acid.

Melting point: 274°–275° C.

EXAMPLE 12

2-(4-Methylphenyl)-4,5,6,7-tetrahydrofuro[2,3-c]pyridine and its hydrochloride 8.5 g (0.025 mole) of the compound prepared according to Example 8 are dissolved in a solution of 100 ml of acetic acid and 100 ml of water, 250 mg of palladinised charcoal (5% of palladium) are added and the mixture is subjected to hydrogenation at approximately 0.35 Mpa for 7 hours at 50° C.

The catalyst is separated, the filtrate is evaporated, the base is liberated from the residue with 1N ammonia solution in ethyl acetate, the organic phase is decanted and evaporated, the base is purified, eluting on silica with a chloroform/methanol mixture and dissolved in 40 ml of ethanol, and 40 ml of ethanol containing 1% of concentrated hydrochloric acid are added. The precipitate is recrystallised and dried.

Melting point: 250°-252° C.

EXAMPLE 13

2-(4-Aminophenyl)-4,5,6,7-tetrahydrofuro[2,3-c]pyridine and its hydrochloride (a) The anion of ethyl 3-oxo-1-phenylmethyl-4-piperidinecarboxylate is prepared according to Example 1(a) above, from 30.7 g (0.1 mole) of 4-[(2-ethoxy-2-oxoethyl)(phenylmethyl)amino]butanoate in 700 ml of toluene and 5 g (0.1 mole) of 50% strength sodium hydride.

(b) The solution thus obtained is cooled, 24.4 g (0.1 mole) of 1-bromo-4'-nitroacetophenone are added and the mixture is stirred overnight at room temperature. The mixture is then washed with 200 ml of water, the slight precipitate is filtered off, and the organic phase is separated and evaporated. An oil remains.

(c) To this oil are added 40 ml of ethanol and 500 ml of concentrated hydrochloric acid, and the mixture is heated under reflux and, after 1 h 30 min, is cooled, and a first fraction of precipitate is isolated. The mixture is reheated under reflux for 1 h and a second fraction of precipitate is precipitated, and, after a third reheating, a third fraction is collected. The three batches are combined, washed with acetone and then ether, and dried.

Melting point: 254° C.

(d) 5.6 g of the above compound are introduced into a mixture of 55 ml of acetic acid and 55 ml of water, 560 mg of palladinised charcoal (5% of palladium) are added and hydrogenation is performed at 0.35 Mpa at room temperature for 15 min, and then at 50° C. for 1 hour. The catalyst is separated by filtration, the filtrate evaporated and the residue taken up in 100 ml of ether. Ammonia solution is added to liberate the base, the organic phase is collected, dried and evaporated, and the residual oil is purified by chromatography on silica, eluting with an 8:2-dichloromethane/methanol mixture. The purified base melts at 160° C. It is dissolved in a mixture of 30 ml of ethanol and 20 ml of ether, some slight turbidity is filtered off and 0.5 ml of concentrated hydrochloric acid is added, with 15 minutes' stirring. The precipitate formed is filtered, washed with ether and recrystallised in a mixture of 40 ml of ethanol and 15 ml of water, with 1% of concentrated hydrochloric acid, and the crystals formed are collected and dried.

Melting point: 258°-260° C.

EXAMPLE 14

2-(4-Chlorophenyl)-4,5,6,7-tetrahydrofuro[2,3-c]pyridine and its hydrochloride (a) 85.1 g, equivalent to 76 ml (1 mole), of 2-pyrrolidone are dissolved in 700 ml of toluene and 50 g (1 mole) of 50% strength sodium hydride in mineral oil are added in 10-g fractions over 1 h in an ice bath. The mixture is stirred for a further 1 h at room temperature and then, again in an ice bath, 106 ml (1 mole) of ethyl chloroacetate dissolved in 200 ml of toluene are added slowly over 30 min. Stirring is maintained for 1 h and 300 ml of water are then added. The mixture is stirred, and the organic phase separated, washed with 200 ml of water, dried and evaporated. An oil remains.

(b) A mixture of 110 g of the above oil, 250 ml of concentrated hydrochloric acid and 250 ml of water are heated under reflux for 6 h. The mixture is left to stand overnight, heated for a further 8 h under reflux and left to stand for 2 days.

The solution is washed with petroleum ether and evaporated, and the residue dried. The dry residue is taken up in 400 ml of ethanol, and the mixture is saturated with gaseous hydrogen chloride and heated under reflux for 5 h. After the mixture has been left overnight undisturbed, the alcohol is evaporated. Ethyl 4-[(2-ethoxy-2-oxoethyl)amino]butanoate chloride remains in the form of a syrupy oil.

(c) A solution of 150 g of potassium carbonate in 200 ml of water, placed in an ice bath, is stirred vigorously, and the above oil is poured slowly into this solution. 100 ml of water are then added, and the liberated base is extracted twice with 200 ml of ether. The organic phases are combined, washed and dried, and the ether driven off.

The residual oil is dissolved in 200 ml of pyridine and 40 ml of benzoyl chloride are added dropwise, while the temperature is maintained below 30° C.

After the addition, the mixture is heated for 1 h at 80° C. and then evaporated, and the residue is taken up in 200 ml of 1N aqueous hydrochloric acid solution and extracted with ethyl acetate. After the organic phase has been washed, dried and evaporated, ethyl 4-[(2-ethoxy-2-oxoethyl)(phenylcarbonyl)amino]butanoate remains in the form of oil.

(d) 16 g of this oil are dissolved in 160 ml of anhydrous toluene, 2.5 g of 50% strength sodium hydride in oil are added and the mixture is heated under reflux. After 10 min, 10 ml of anhydrous ethanol are added dropwise and the solution is heated under reflux for 7 h and then cooled in an icebath. 11.7 g of 1-bromo-4'-chloroacetophenone are then added and the mixture is stirred overnight at room temperature.

The mixture is washed with 30 ml of water, the organic phase is separated and evaporated, the residue taken up in 20 ml of ethanol and 250 ml of concentrated hydrochloric acid, and the mixture is heated for 2 h 30 min under reflux. The mixture is then cooled in an ice bath while being stirred, and this causes a brown precipitate to form. The latter is filtered, taken up in 50 ml of acetone and stirred in ice. The solid is separated, the acetone is driven off, and the residue is taken up in 50 ml of ethyl acetate, separated and added to the first solid collected. It is dried, then recrystallised in 98% strength ethanol containing 1% of concentrated hydrochloric acid, and dried.

Melting point: 267°-269° C.

EXAMPLE 15

2-(4-Methylphenyl)-6-methyl-4,5,6,7-tetrahydrofuro[2,3-c]pyridine and its hydrochloride 4 g of the compound obtained according to Example 12 are introduced into a mixture of ethyl acetate and ammonia solution, and the base is liberated by stirring the mixture, isolating the organic phase and evaporating the solvent.

1.75 g of the evaporation residue is introduced into a mixture of 3 ml of formic acid and 3 ml of 40% strength formaldehyde, and the mixture is heated to 100° C. on an oil bath for 30 min. The mixture is allowed to cool, poured into 100 ml of ice and extracted with ethyl acetate. After being washed and dried and evaporation of the solvent, an oil remains which is purified by chromatography on a silica column, eluting with acetone. The pure base is dissolved in 40 ml of ether, some slight turbidity is removed by filtration and ethanol saturated with hydrogen chloride gas is added to the filtrate. The mixture is stirred for 10 min at room temperature, and the precipitate is filtered and recrystallised in 40 ml of ethanol to which a few drops of water are added until dissolution is complete. After recrystallisation, the product is washed with ether and dried.

Melting point: 270°–272° C.

EXAMPLE 16

2-(4-Bromophenyl)-6-ethyl-4,5,6,7-tetrahydrofuro[2,3-c]pyridine and its hydrochloride The base is liberated from the compound of Example 11, 2.2 g of this are introduced into 25 ml of acetic anhydride and the mixture is stirred overnight at room temperature. The suspension obtained is poured into 150 ml of ice, the mixture is extracted with ethyl acetate, the organic phase is washed with ammonia solution and then water, the solvent is evaporated and the residue is dried by azeotropic entrainment with toluene.

A suspension of 0.25 g of aluminium chloride and 0.5 g of lithium aluminium hydride is prepared in 25 ml of anhydrous tetrahydrofuran, cooled in an ice bath, and added dropwise to a solution of 2.4 g of the above dry residue in 25 ml of dry tetrahydrofuran. After the addition is complete, the mixture is stirred for a further 15 min and 5 ml of water, followed by 100 ml of ethyl acetate are then added slowly. Water is then added in small portions until the aluminium and lithium hydroxides have become pasty, and the organic phase is separated by filtration and evaporated. A solid residue remains and this is dried by azeotropic entrainment with toluene, and then purified by chromatography on a silica column, eluting with an 8:2-dichloromethane/methanol mixture. The purified base is dissolved in 50 ml of ether and 3 ml of ethanol saturated with hydrogen chloride are added. The mixture is stirred for 10 min, and the precipitate is filtered, recrystallised in absolute ethanol, washed with ether and dried.

Melting point: 262°–264° C.

The table below illustrates the structures and physical properties of various compounds according to the invention.

TABLE

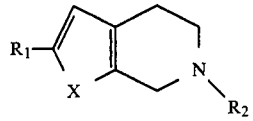

(I)

| Compound | Example | X | R1 | R2 | Base/salt | M.p. °C. |
|---|---|---|---|---|---|---|
| 1 | 1 | NH | $C_6H_5-$ | $-CH_2-C_6H_5$ | HCl | 236–238 |
| 2 | 2 | NH | $4-CH_3O-C_6H_4-$ | $-CH_2-C_6H_5$ | HCl | 237–238 |
| 3 |  | NH | $4-CH_3-C_6H_4-$ | $-CH_2-C_6H_5$ | HCl | 246–248 |
| 4 | 3 | NH | $4-Br-C_6H_4-$ | $-CH_2-C_6H_5$ | HCl | 264–266 |
| 5 |  | NH | $3-CH_3O-C_6H_4-$ | $-CH_2-C_6H_5$ | HCl | 216–218 |
| 6 |  | NH | $4-Cl-C_6H_4-$ | $-CH_2-C_6H_5$ | HCl | 257–259 |
| 7 | 4 | NH | $4-F-C_6H_4-$ | $-CH_2-C_6H_5$ | HCl | 246–248 |
| 8 |  | NH | 2-naphthyl | $-CH_2-C_6H_5$ | HCl | 236–238 |
| 9 | 5 | NH | $4-CH_3O-C_6H_4$ | H | HCl | 235 |
| 10 | 6 | NH | $C_6H_5-$ | H | Base | 179–181 |
|  |  |  |  |  | HCl | 249–251 |
| 11 |  | O | $C_6H_5-$ | $-CH_2-C_6H_5$ | HCl | 244–245 |
| 12 | 7 | O | $4-CH_3O-C_6H_4-$ | $-CH_2-C_6H_5$ | HCl | 252–253 |
| 13 | 8 | O | $4-CH_3-C_6H_4-$ | $-CH_2-C_6H_5$ | HCl | 251–253 |
| 14 |  | O | $3-CH_3O-C_6H_4-$ | $-CH_2-C_6H_5$ | HCl | 219–221 |
| 15 | 9 | O | $4-Br-C_6H_4-$ | $-CH_2-C_6H_5$ | HCl | 263–265 |
| 16 |  | O | $4-Cl-C_6H_4-$ | $-CH_2-C_6H_5$ | HCl | 265–267 |
| 17 |  | O | $4-F-C_6H_4-$ | $-CH_2-C_6H_5$ | HCl | 248–250 |
| 18 |  | O | $C_6H_5$ | H | HCl | 255–257 |
| 19 |  | O | $4-C_6H_5-C_6H_4-$ | $-CH_2-C_6H_5$ | HCl | 270–272 |
| 20 | 10 | O | $4-CH_3O-C_6H_4-$ | H | HCl | 226–228 |
| 21 | 11 | O | $4-Br-C_6H_4-$ | H | HCl | 274–275 |
| 22 | 12 | O | $4-CH_3-C_6H_4-$ | H | HCl | 250–252 |
| 23 |  | O | 2-naphthyl | $-CH_2-C_6H_5$ | HCl | 249–251 |
| 24 |  | O | $3,4-Cl_2-C_6H_3-$ | H | HCl | 261–263 |
| 25 |  | O | 2-naphthyl | H | HCl | 265–267 |
| 26 |  | O | $4-F-C_6H_4-$ | H | HCl | 254–255 |
| 27 |  | O | $3-CH_3-C_6H_4-$ | H | HCl | 257–259 |
| 28 |  | O | $2-CH_3-C_6H_4-$ | H | HCl | 245–247 |
| 29 |  | O | $3-CF_3-C_6H_4-$ | H | HCl | 273–275 |
| 30 |  | O | $2-F-C_6H_4-$ | H | HCl | 284–286 |
| 31 |  | O | $3-F-C_6H_4-$ | H | HCl | 258–260 |
| 32 | 14 | O | $4-Cl-C_6H_4-$ | H | HCl | 267–269 |
| 33 |  | O | (methylenedioxyphenyl) | H | HCl | 260–262 |
| 34 |  | O | $4-C_2H_5-C_6H_4-$ | H | HCl | 235–237 |

TABLE-continued $$\text{(I)}$$

(structure: R1—X—[bicyclic ring with N—R2])

| Compound | Example | X | R1 | R2 | Base/salt | M.p. °C. |
|---|---|---|---|---|---|---|
| 35 | 13 | O | 4-NH$_2$—C$_6$H$_4$— | H | HCl | 258–260 |
| 36 |  | O | 3-C$_2$H$_5$—C$_6$H$_4$— | H | HCl | 225–226 |
| 37 |  | O | 3-NH$_2$—C$_6$H$_4$— | H | 2HCl | >300 |
| 38 | 15 | O | 4-CH$_3$—C$_6$H$_4$— | —CH$_3$ | HCl | 270–272 |
| 39 |  | O | 4-CH$_3$—C$_6$H$_4$— | —CH$_2$CH$_3$ | HCl | 250–252 |
| 40 |  | O | C$_6$H$_5$— | —CH$_3$ | HCl | 263–265 |
| 41 |  | O | C$_6$H$_5$— | —CH$_2$CH$_3$ | HCl | 237–239 |
| 42 |  | O | 4-F—C$_6$H$_4$— | —CH$_3$ | HCl | 250–252 |
| 43 |  | O | 4-F—C$_6$H$_4$— | —CH$_2$CH$_3$ | HCl | 263–265 |
| 44 |  | O | 4-Br—C$_6$H$_4$— | —CH$_3$ | HCl | 291–293 |
| 45 | 16 | O | 4-Br—C$_6$H$_4$— | —CH$_2$CH$_3$ | HCl | 262–264 |

The compounds of the invention were subjected to pharmacological trials.

The toxicity (lethal dose 50, LD$_{50}$) of the compounds was determined in CD1 strain mice by a graphic method. The LD$_{50}$ values range from 100 to 1000 mg/kg intraperitoneally.

The compounds of the invention were subjected to the total cerebral ischaemia test. The ischaemia is due to a cardiac arrest induced by a rapid intravenous injection of MgCl$_2$. In this test, the "survival time", that is to say the interval between the time of injection of MgCl$_2$ and the last observable respiratory movement of each mouse, is measured. This latter movement is taken as the final index of functioning of the central nervous system. The respiratory arrest appears approximately 19 seconds after the injection of MgCl$_2$.

Male mice (Charles River CD1) are studied in groups of 10.

The mice are supplied with food and water ad libitum before the trials. The survival time is measured 10 minutes after the intraperitoneal administration of the compounds of the invention. The results are given in the form of difference between the survival time measured in a group of 10 mice which have received the compound and the survival time measured in a group of 10 mice which have received the vehicle liquid. The ratios between the modifications in the survival term and the dose of the compound are recorded graphically according to a semi-logarithmic curve.

This curve permits calculation of the 3-second effective dose (ED$_{3''}$), that is to say the dose (in mg/kg) which produces an increase of 3 seconds in the survival time relative to the control group of 10 untreated mice. An increase of 3 seconds in the survival time is both statistically significant and reproducible.

The ED$_{3''}$ values of the compounds of the invention range from 6 to 60 mg/kg i.p.

The compounds of the invention were also subjected to the hypobaric hypoxia test.

CD1 strain mice are maintained in an atmosphere which is depleted in oxygen by production of a partial vacuum (190 mm of mercury, corresponding to 5.25% of oxygen). The survival time of the animals is noted. This time is increased by agents capable of promoting tissue oxidation, and particularly cerebral oxidation. The compounds studied are administered intraperitoneally at several doses, 10 minutes before the trial. The percentage increases in the survival time relative to values obtained with control animals are calculated.

The average active dose (AAD), the dose which increases the survival time by 100%, is determined graphically. The AAD of the compounds of the invention is from 10 to 32 mg/kg intraperitoneally.

The compounds of the invention were also the subject of a trail of [$^3$H]-imipramine binding to whole rat cortex.

The preparation of the tissue comprises:

(a) homogenisation in 50 volumes (per gramme of tissue) of incubation buffer, followed by centrifugation at 20,000 rpm for 10 min.

(b) Repetition of the above operation with the centrifugation pellet.

(c) Taking up the final pellet in 33 volumes (per gramme of tissue) of the incubation buffer, giving a suspension of 30 mg of tissue per ml.

The incubation buffer contains, per liter, 120 millimoles of sodium chloride, 50 millimoles of Tris and 5 millimoles of potassium chloride, and has a pH of 7.4 at 0° C. To determine the total binding, the following are introduced in each incubation tube:

100 μl of cortex membrane, 30 mg/ml,
150 μl of buffer, and
50 μl of [$_3$H]-imipramine.

To determine the non-specific binding, the following are introduced in each incubation tube:

100 μl of cortex membrane, 30 mg/ml,
140 μl of buffer,
10 μl of desipramine, 30×10$^{-4}$ moles/l, and
50 μl of [$^3$H]-imipramine.

For displacement by the substances to be studied, the concentration of [$^3$H]-imipramine is 2.5 nM, and those of the active substances range up to 100 μM.

The incubation is performed at 0° C. for 1 hour.

To assess the activity of the compounds, a curve is established for percentage inhibition of the specific [$^3$H]-imipramine binding as a function of the concentration of displacing drug. The IC$_{50}$ is the concentration of displacing drug which inhibits 50% of the specific [$^3$H]-imipramine binding (graphic determination) at a tritiated ligand concentration of 2.5 nM.

The IC$_{50}$ concentrations of the compounds of the invention are mostly situated at less than 100 μM, and are as low as 0.01 μM for some of them.

Finally, the compounds of the invention were the subject of a trial in respect of their inhibition of noradrenaline capture and serotonin capture in a preparation of unpurified rat-hypothalamus synaptosomes, a trial suggested by the method of Ross S. B. and Renyi A. L. (Acta Pharmacolog. Toxicol. 36, 382-394, 1975).

Each incubation mixture contains 0.1 nmol of [$^3$H]-noradrenaline, 0.1 nmol of [$^{14}$C]-serotonin, 100 μl of the preparation of unpurified synaptosomes (corresponding to 10 mg of initial cerebral tissue), the compound to be studied and 1.8 ml of Krebs-Henseleit buffer (pH 7.4, 1.25 μmol of nialamide, 114 μmol of ascorbic acid, 59.5 μmol of disodium EDTA and 1,111 μmol of glucose per 100 ml of buffer). The capture process is triggered by adding the labelled amines, and the incubation is performed for 5 min in centrifuge tubes maintained at 37° C. The reaction is interrupted by filtering the incubation medium on 0.45 μm millipore MF (mixture of cellulose esters) filters (ref HAWP 02500), and then rinsing with 2.5 ml of physiological serum. The dry filters, which have retained the synaptosomes, are then introduced into scintillation vials, and 10 ml of scintillation liquid (Aquasol-NEN) are added. The vials are left standing for 2 hours, during which the filters are dissolved, and the radioactivity is then measured.

The effective capture is obtained by deducting the passive capture under the same conditions but in ice. The inhibition of capture is determined as a percentage of the effective capture, with and without the compound to be studied, in the same trial. The IC$_{50}$ concentration, that is to say the concentration (in μM) which causes 50% inhibition, is established from a logarithmic curve of the response as a function of the concentration.

The IC$_{50}$ concentration of the compounds of the invention ranges from 0.23 to 10 μM in the case of noradrenaline and from 0.08 to 10 μM in the case of serotonin.

pharmacological study of the compounds of the invention shows that they possess antianoxic activity, and that they can be used in therapy for treating disorders of alertness, in particular to combat behaviour disorders attributable to cerebral vascular damage and to cerebral sclerosis in geriatrics, as well as for treating metabolic encephalopathies and treating depressive states.

The invention consequently comprises all pharmaceutical compositions containing the compounds and/or their salts as active principles, in combination with any excipients suitable for their administration, especially orally or parenterally.

The administration routes can be the oral and parenteral routes.

The daily dosage can range from 1 to 100 mg parenterally and from 5 to 500 mg orally.

We claim:
1. A pyridine derivative of the formula (I)

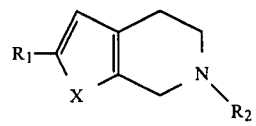

in which X is —O— or —NH—, R$_1$ is a phenyl group optionally substituted by one or two halogen atoms or by a methyl, ethyl, trifluoromethyl, methoxy or phenyl group or, when R$_2$ is not a benzyl group, an amino group, or is a naphthyl or benzodioxanyl group, and R$_2$ is a hydrogen or a benzyl group, or when X is —O—, R$_2$ can also be a methyl or ethyl group, and a pharmaceutically acceptable acid addition salt thereof.

2. A compound according to claim 1, wherein R$_2$ is hydrogen.

3. A compound according to claim 1, wherein X is —O— and R$_2$ is methyl or ethyl.

4. A composition for treating anoxia comprising a pyridine derivative of the formula (I) or a pharmaceutically acceptable salt thereof as claimed in claim 1 in an amount effective in treating anoxia, and a pharmaceutically acceptable excipient.

5. A composition for treating metabolic encephalopathy, comprising a pyridine derivative of the formula (I) or a pharmaceutically acceptable salt thereof as claimed in claim 1 in an amount effective for treating metabolic encephalopathy, and a pharmaceutically acceptable excipient.

6. A pharmaceutical composition for treating depression, comprising a pyridine derivative of the formula (I) or a pharmaceutically acceptable salt thereof as claimed in claim 1 in an amount effective for treating depression, and a pharmaceutically acceptable excipient.

7. A method for treating anoxia in a subject, comprising administering to the subject a pyridine derivative of the formula (I) or a pharmaceutically acceptable salt thereof as claimed in claim 1 in an amount effective for treating anoxia in the subject.

8. A method for treating metabolic encephalopathy in a subject, comprising administering to the subject a pyridine derivative of the formula (I) or a pharmaceutically acceptable salt thereof as claimed in claim 1 in an amount effective for treating metabolic encephalopathy in the subject.

9. A method for treating depression in a subject, comprising administering to the subject a pyridine derivative of the formula (I) or a pharmaceutically acceptable salt thereof as claimed in claim 1 in an amount effective for treating depression in the subject.

* * * * *